United States Patent
Zhao et al.

(10) Patent No.: US 11,097,263 B2
(45) Date of Patent: Aug. 24, 2021

(54) AROMATIZATION CATALYST, PREPARATION METHOD, REGENERATION METHOD THEREOF, AND AROMATIZATION METHOD

(71) Applicant: CHINA UNIVERSITY OF PETROLEUM—BEIJING, Beijing (CN)

(72) Inventors: Liang Zhao, Beijing (CN); Jinsen Gao, Beijing (CN); Tianzhen Hao, Beijing (CN); Lixia Dong, Beijing (CN); Di Gao, Beijing (CN); Xiaoyu Wu, Beijing (CN); Xiaoqin Wang, Beijing (CN); Liyuan Cao, Beijing (CN); Chunming Xu, Beijing (CN)

(73) Assignee: CHINA UNIVERSITY OF PETROLEUM—BEIJING, Beijing (CN)

( * ) Notice: Subject to any disclaimer, the term of this patent is extended or adjusted under 35 U.S.C. 154(b) by 0 days.

(21) Appl. No.: 16/557,968

(22) Filed: Aug. 30, 2019

(65) Prior Publication Data
US 2021/0060540 A1    Mar. 4, 2021

(51) Int. Cl.
*B01J 29/40* (2006.01)
*B01J 37/02* (2006.01)
(Continued)

(52) U.S. Cl.
CPC ......... *B01J 37/0213* (2013.01); *B01J 29/061* (2013.01); *B01J 29/064* (2013.01); *B01J 29/068* (2013.01); *B01J 29/072* (2013.01); *B01J 29/076* (2013.01); *B01J 29/40* (2013.01); *B01J 29/405* (2013.01); *B01J 29/42* (2013.01); *B01J 29/44* (2013.01); *B01J 29/46* (2013.01); *B01J 29/48* (2013.01); *B01J 29/83* (2013.01); *B01J 29/84* (2013.01); *B01J 29/85* (2013.01); *B01J 35/002* (2013.01); *B01J 35/0006* (2013.01); *B01J 35/023* (2013.01); *B01J 35/1057* (2013.01); *B01J 35/1085* (2013.01); *B01J 37/0009* (2013.01); *B01J 37/02* (2013.01); *B01J 37/0201* (2013.01); *B01J 37/0205* (2013.01); *B01J 37/0207* (2013.01); *B01J 37/0209* (2013.01); *B01J 37/0236* (2013.01); *B01J 37/10* (2013.01); *B01J 37/28* (2013.01); *B01J 37/30* (2013.01); *B01J 2229/18* (2013.01); *B01J 2229/183* (2013.01); *B01J 2229/186* (2013.01); *B01J 2229/20* (2013.01); *B01J 2229/24* (2013.01); *B01J 2229/36* (2013.01); *B01J 2229/42* (2013.01); *C07C 2527/14* (2013.01); *C07C 2527/185* (2013.01); *C07C 2527/186* (2013.01); *C07C 2527/187* (2013.01);
(Continued)

(58) Field of Classification Search
CPC ...... B01J 29/061; B01J 29/064; B01J 29/068; B01J 29/072; B01J 29/076; B01J 29/405; B01J 29/42; B01J 29/46; B01J 29/44; B01J 29/48; B01J 29/83; B01J 29/84; B01J 29/85; B01J 2229/18; B01J 2229/183; B01J 2229/186; B01J 2229/20; B01J 2229/24; B01J 2229/36; B01J 2229/42; B01J 35/0006; B01J 35/002; B01J 35/023; B01J 35/1057; B01J 35/1085; B01J 37/0009; B01J 37/02; B01J 37/0201; B01J 37/0205; B01J 37/0209; B01J 37/10; B01J 37/28; B01J 37/30; C07C 2529/068; C07C 2529/072; C07C 2529/076; C07C 2529/40; C07C 2529/44; C07C 2529/46; C07C 2529/48; C07C 2529/83; C07C 2529/84; C07C 2529/85; C07C 2527/14; C07C 2527/185; C07C 2527/186; C07C 2527/87; C07C 2527/187; C10G 35/095; C10G 45/64; C10G 45/68; C10G 2400/20
USPC ........ 502/60, 63, 64, 65, 66, 69, 71, 73, 74, 502/77, 85
See application file for complete search history.

(56) References Cited

U.S. PATENT DOCUMENTS

| | | | | |
|---|---|---|---|---|
| 5,898,089 A | * | 4/1999 | Drake | ...... B01J 23/06 208/134 |
| 2006/0004238 A1 | * | 1/2006 | Kelly | ...... B01J 29/90 585/467 |

(Continued)

FOREIGN PATENT DOCUMENTS

| | | | |
|---|---|---|---|
| CN | 1057476 A | | 1/1992 |
| CN | 1586721 A | * | 3/2005 |

(Continued)

OTHER PUBLICATIONS

Shenglin et al., Machine Translation of CN 101530813, 2009, pp. 1-16.*

*Primary Examiner* — Elizabeth D Wood
(74) *Attorney, Agent, or Firm* — J.C. Patents

(57) ABSTRACT

The present disclosure provides an aromatization catalyst, a preparation method, a regeneration method and an aromatization method thereof. The preparation method comprises steps of: mixing a zeolite molecular sieve with a binder to obtain a catalyst precursor; the catalyst precursor is successively subjected to an ion exchange modification and a first modification treatment, and then subjected to a hydrothermal treatment, and further subjected to active metal loading and a second modification treatment, to obtain the aromatization catalyst. The aromatization catalyst has good carbon deposition resistance and high aromatization activity, and enables an aromatization reaction to be completed under mild conditions, and has high aromatic selectivity, and the liquid yield is above 98.5%.

5 Claims, No Drawings

(51) Int. Cl.
*B01J 37/00* (2006.01)
*B01J 37/10* (2006.01)
*B01J 37/30* (2006.01)
*B01J 29/064* (2006.01)
*B01J 29/076* (2006.01)
*B01J 29/06* (2006.01)
*B01J 29/068* (2006.01)
*B01J 29/072* (2006.01)
*B01J 29/42* (2006.01)
*B01J 29/83* (2006.01)
*B01J 29/85* (2006.01)
*B01J 29/84* (2006.01)
*B01J 29/44* (2006.01)
*B01J 29/46* (2006.01)
*B01J 29/48* (2006.01)
*B01J 35/00* (2006.01)
*B01J 35/10* (2006.01)
*B01J 35/02* (2006.01)
*B01J 37/28* (2006.01)
*C10G 45/64* (2006.01)
*C10G 35/095* (2006.01)
*C10G 45/68* (2006.01)

(52) U.S. Cl.
CPC .. *C07C 2529/068* (2013.01); *C07C 2529/072* (2013.01); *C07C 2529/076* (2013.01); *C07C 2529/40* (2013.01); *C07C 2529/44* (2013.01); *C07C 2529/46* (2013.01); *C07C 2529/48* (2013.01); *C07C 2529/83* (2013.01); *C07C 2529/84* (2013.01); *C07C 2529/85* (2013.01); *C10G 35/095* (2013.01); *C10G 45/64* (2013.01); *C10G 45/68* (2013.01); *C10G 2400/20* (2013.01)

(56) References Cited

U.S. PATENT DOCUMENTS

2016/0288108 A1* 10/2016 Khanmamedova ..... C07C 15/02
2017/0144948 A1* 5/2017 Stevenson .............. C10G 45/68

FOREIGN PATENT DOCUMENTS

| CN | 1586721 A | 3/2005 |
| CN | 101530813 A | 9/2009 |
| CN | 106552663 A | 4/2017 |

* cited by examiner

AROMATIZATION CATALYST, PREPARATION METHOD, REGENERATION METHOD THEREOF, AND AROMATIZATION METHOD

TECHNICAL FIELD

The present disclosure relates to the technology field of catalyst processing and regeneration and, in particular, to an aromatization catalyst, a preparation method, a regeneration method thereof, and an aromatization method.

BACKGROUND

The discovered petroleum resources around the world are becoming more heavier in quality, and the production of clean oil products is becoming more difficult, with the increasing impact of automobile exhaust emission on atmospheric environment, requirements for the quality of motor gasoline in countries in the world are becoming more stringent. Since Jan. 1, 2019, China intends to perform the National VI motor gasoline standard, which makes stricter regulations on indicators such as sulfur content and olefin content, and the like.

In China's gasoline pool, fluid catalytic cracking gasoline accounts for up to 75%, meanwhile since a fluid catalytic cracking gasoline (FCC gasoline) has a composition characteristic of high olefins, about 90% of olefins in a commercial gasoline come from the fluid catalytic cracking gasoline, therefore, reducing olefin content in the fluid catalytic cracking gasoline so as to reduce olefin content in the commercial gasoline is a main approach to produce gasoline that meets the National VI standard at present.

In the existing methods for reducing olefins, FCC gasoline aromatization is a well-recognized solution at present, due to the high olefin content of FCC gasoline, and the synthesis or preparation of an aromatization catalysts used in an aromatization reaction has become a very important branch.

CN91105256.9 disclosed a zinc-containing zeolite catalyst for low olefins, which involving loading a zinc-containing compound on a ZSM-5 zeolite, thereby effectively avoiding zinc loss, but the aromatic hydrocarbon yield was low, no more than 45%. And when the aromatization catalyst was used, an aromatization reaction needs to be completed at high temperatures above 400° C., such as 500~550° C., and the energy required for the reaction was high.

CN200410050202.3 disclosed an aromatization catalyst of $C_4$ liquefied gas and preparation method thereof. The catalyst was prepared by: mixing a nano-sized ZSM-5 molecular sieve with alumina and molding, and then exchanging with an ammonium ion solution to form a hydrogen-type catalyst, and then sequentially treating the hydrogen-type catalyst with water vapor and an acid solution, and the resulting catalyst may be subjected to aromatization in a fixed bed reactor under the conditions of 300° C.~500° C., 0.1 Mpa~5 Mpa, a feed space velocity of 0.05 $h^{-1}$ to 20 $h^{-1}$, and no loader gas. The aromatization effect was good, but the liquid yield was not high, and steps were complicated, resulting in a lot of work during the operation process.

CN200810010622.7 disclosed a molecular sieve catalyst for aromatization reaction of $C_4$ liquefied gas, a metal-zinc-loaded rare earth-ZSM-5/ZSM-11 co-crystal molecular sieve was used, and alumina was added as a binder, a hydrogen-type molecular sieve was formed at first, and then subjected to a high temperature hydrothermal treatment, and then loaded with metal zinc by an impregnated method, and finally calcined at a high temperature. The activity of an aromatization reaction using the molecular sieve catalyst was enhanced, the reaction stability was improved, and the liquid yield thereof was 60% 70%, but the aromatization reaction temperature was above 480° C., thus the aromatization reaction needs a high energy consumption.

CN201510618018.2 disclosed a preparation method of a straight-run naphtha aromatization catalyst, in this patent the catalyst was modified through a ZSM-5 molecular sieve, and an active metal was loaded, resulting in corresponding catalytic activity and aromatic hydrocarbon selectivity were obtained in a product. However, additive modification and active metal loading carried out by the method were aimed at the aromatization of raw materials with a higher alkane content, while for the aromatization of olefins, the effect was modest.

In addition, aromatization catalysts described in other literatures generally have difficulty in balancing the liquid yield and the selectivity for converting olefins to aromatics, usually the liquid yield may be up to 60~70%, while in order to pursue high selectivity, the liquid yield is often given up. However, in actual production the liquid yield mentioned above will inevitably causes a large amount of loss in petroleum products, which seriously affects the production benefit and economic benefit of an enterprise, and which is also one of the factors that limit practical application of the aromatization catalyst. Moreover, the existing aromatization catalyst has a low catalytic activity, and generally an aromatization reaction needs to be completed at 450° C. or a higher temperature, while in order to pursue high liquid yield or high selectivity, means of further increasing aromatization reaction temperature are taken, thus generating a lot of energy consumption. At the same time, most of the aromatization catalysts have a short service life, so the industrial amplification adaptability is poor, which further restricts the application of the aromatization catalyst. So far, there is no good aromatization catalyst to overcome the above various shortcomings.

SUMMARY

In view of the above defects in the prior art, the present disclosure provides an aromatization catalyst and a preparation method thereof, and the aromatization catalyst prepared by the preparation method has good carbon deposition resistance, thus has a long service life. The aromatization catalyst has high aromatization activity, enables an aromatization reaction to be stably completed under mild conditions, and also has high aromatic selectivity while maintaining a very high liquid yield.

The present disclosure also provides an aromatization method, which is carried out by using the above aromatization catalyst. The aromatization method may stably run for a long period of time under mild conditions, and also has high aromatic selectivity while maintaining a very high liquid yield.

The present disclosure also provides a method for regenerating an aromatization catalyst, wherein the aromatization catalyst being subjected to an aromatization reaction can be regenerated by a simple oxidation-reduction, and the regenerated aromatization catalyst still keeps the above advantages.

In order to achieve the above objects, the present disclosure first provides a method for preparing an aromatization catalyst, comprising steps of: mixing a zeolite molecular sieve with a binder at a dry basis weight ratio of (1:9) (9:1) to obtain a catalyst precursor;

the catalyst precursor is successively subjected to an ion exchange modification and a first modification treatment, then subjected to a hydrothermal treatment, and further subjected to active metal loading and a second modification treatment, to obtain the aromatization catalyst; wherein an exchange element used for the ion exchange modification is at least one alkali metal selected from Group IA of the Periodic Table of the Elements, with a loading amount of 0.1~2 wt % based on the exchange element;

a first modifying element used in the first modification treatment is at least one element selected from Group IA, Group VA, and lanthanide metals of the Periodic Table of the Elements, with a loading amount of 0.05~10 wt % based on the first modifying element;

the active metal is at least one element selected from Group VIIB, Group VIII, Group IB and Group IIB of the Periodic Table of the Elements, with a loading amount of 0.5~25 wt % based on the active metal;

a second modifying element used for the second modification treatment is at least one element selected from Group VA and the lanthanide metals of the Periodic Table of Elements, with a loading amount of 0.05~10 wt % based on the second modifying element.

Specifically, in an actual production process, the zeolite molecular sieve is generally selected from hydrogen-type zeolite molecular sieves, a silica-alumina ratio (Si/Al ratio) thereof is usually 1~300, the zeolite molecular sieve thus has a suitable acid amount and acid strength. The zeolite molecular sieve can be at least one of the commonly used HZSM-5 zeolite molecular sieve, HZSM-8 zeolite molecular sieve and HZSM-11 zeolite molecular sieve.

In an embodiment of the present disclosure, the zeolite molecular sieve that specifically used may be a nano molecular sieve, i.e. a molecular sieve having a crystal grain size of less than 0.1 μm, and the nano molecular sieve has a larger surface area and a shorter pore channel than a conventional micron-sized molecular sieve.

The above binder may be a conventional binder in the art, such as pseudoboehmite or alumina. In a specific embodiment of the present disclosure, pseudoboehmite is generally used as the binder.

The mixing of the zeolite molecular sieve with the binder may be completed by a conventional physical mixing in the art. The resulting catalyst precursor is actually used as a catalyst carrier for subsequent active metal loading and modification treatment. In a specific embodiment of the present disclosure, the zeolite molecular sieve and the pseudoboehmite are mixed at a dry basis weight ratio of (1-9):1, so that the finally prepared aromatization catalyst has more suitable acidity.

The inventors have found that the ion exchange modification performed on the catalyst precursor may adjust internal structural electron cloud density and acid strength of the catalyst carrier, thereby facilitating active metal loading and catalytic performance of a catalyst. The inventors have found that the aromatization catalyst obtained after the ion exchange modification has greatly prolonged single-pass life e.g. single-pass activity is 8~10 days while the high aromatization activity can be maintained.

The ion exchange modification may be completed by a conventional ion exchange process in the art. For example, it may be carried out by adding an ion exchange solution to the catalyst precursor, and after the catalyst precursor being treated with the ion exchange solution under a constant temperature water bath for a period of time, further suction filtrating the treated catalyst precursor under room temperature, and drying, calcining the treated catalyst precursor.

In an embodiment of the present disclosure, a salt solution containing sodium ions and/or potassium ions (such as sodium chloride, potassium chloride, etc.) or an alkali solution (such as sodium hydroxide or potassium hydroxide) is used as the ion exchange solution to perform the ion exchange modification on the catalyst precursor, controlling the ion exchange modification is conducted at 60~120° C. for at least 30 minutes, generally 30~180 minutes, to obtain a treated catalyst precursor, and then drying the treated catalyst precursor at 60~280° C. for at least 3 hours, such as 3~15 hours, and finally calcining the treated catalyst precursor at 450~700° C. for at least 1 hour, such as 1~8 hours.

In the process of the ion exchange modification, either one or both of sodium element and potassium element can be introduced. When both of sodium element and potassium element are introduced, they may be introduced synchronously or stepwise. In the stepwise introduction, a salt solution or an alkali solution of the corresponding alkali metal element is selected for each ion exchange modification, and after the each ion exchange modification, drying and calcination need to be performed.

The first modification treatment performed on the catalyst precursor may adjust electron cloud density and acid property of the catalyst carrier, thereby facilitating the dispersion of the active metal, and it may be completed by a conventional modification process in the art, for example, an impregnation method, which using a soluble compound solution of the active metal as an impregnation liquid, and the impregnation liquid is added to the catalyst precursor dropwise, and after the impregnation is completed, an impregnated catalyst precursor is obtained, drying and calcining the impregnated catalyst precursor, then the first modification treatment is completed. In an embodiment of the present disclosure, the first modification treatment is generally performed by an equal volume impregnation method.

In the process of the first modification treatment, one or more of the elements of Group IA, Group VA, and lanthanide metals of the Periodic Table of the Elements may be introduced for modification. When more than two elements are introduced, these elements may be introduced simultaneously, or may be introduced stepwise, for example, a salt solution of two elements are simultaneously introduced for each impregnation, and after the each impregnation, aging, drying, and calcination need to be performed.

In general, the aging during the first modification treatment may be performed at room temperature (20~30° C.) for at least 1 hour. The drying temperature may be controlled at 60~280° C., and the drying time is generally not less than 3 hours. For the comprehensive consideration of production cost and production efficiency, the drying time is generally 3~15 hours. The calcination temperature is generally controlled at 400~650° C., and the calcination time is generally controlled not less than 1 hour, for example, 1~8 hours.

The hydrothermal treatment after the first modification treatment enables the zeolite molecular sieve to remove part of skeleton structure, such that acidity of the aromatization catalyst can be appropriately adjusted. The hydrothermal treatment may employ a conventional hydrothermal treatment process in the art. In an embodiment of the present disclosure, the hydrothermal treatment is controlled to be performed at a temperature of 300~600° C. for at least 1 hour under a water vapor atmosphere. The water vapor generally used is 100% water vapor, and the hydrothermal treatment is performed at a constant temperature of 300~600° for 1~10 hours C.

The active metal loading may be carried out after the hydrothermal treatment, and the active metal used for the active metal loading may be one or more of the metal elements selected from Groups VIIB, VIII, IB and IIB of the Periodic Table of the Elements, such as one or more of Fe, Co, Ni, Ru, Cu, Mn, and Zn, and the like. If two or more active metals are loaded, they may be introduced simultaneously, that is, a metal salt solution containing above two or more active metal elements is used for impregnation, or the impregnation may be performed stepwise, and drying and calcination are carried out after each impregnation.

The inventors have found that an excessive loading amount of the active metal tends to cause a decrease in the selectivity of converting olefins to aromatics. In general, the active metal loading amount may be controlled as 0.5~15 wt %, further 0.5~9 wt %.

For the active metal loading, a metal salt of the active metal may be dissolved with 0.1~1.0 mol/L citric acid aqueous solution so as to prepare an impregnation liquid, and the catalyst precursor is impregnated to realize the active metal loading. In an embodiment of the present disclosure, a mass ratio of the impregnation liquid to the catalyst precursor is generally controlled to be (0.8~3.0):1 to obtain a better dispersion of the active metal, which is advantageous for improving performances of the aromatization catalyst.

The metal salt of the above active metal includes, but is not limited to, soluble salt such as a nitrate, a halate, a sulfate, an acetate, an ammonium salt, and the like. In an embodiment of the present disclosure, the metal salt of the active metal selected is a nitrate or a chloride salt.

The impregnation temperature and time in the active metal loading process are not specifically limited in the present disclosure, and a conventional impregnation temperature and time in the art may be adopted. In an embodiment of the present disclosure, the impregnation is controlled to be performed at a temperature of 0~50° C. for 0.5~18 hours.

In an embodiment of the present disclosure, a mass ratio of the impregnation liquid to the catalyst precursor is generally to be (0.8~2.0): 1; the impregnation temperature is 20~50° C., generally 20~40° C.; and the impregnation time is 2~18 hours, generally 2~12 hours. With the impregnation performed under the above conditions, a better dispersion of active metal may be obtained, thereby optimizing the performances of the finally resulting aromatization catalyst.

After the impregnation is completed, the drying may be proceeded at 50~180° C. for at least 2 hours, and the calcination may be performed at 100~650° C. for at least 2 hours, then the active metal loading is completed. Specifically, the drying temperature is 50~160° C., generally 50~130° C., further 80~130° C.; the drying time is 2~20 hours, generally 4~20 hours, further 6~12 hours; the calcination temperature is 400~650° C., generally 450~650° C., further 450~550° C.; the calcination time is 2~10 hours, generally 3~6 hours.

Further, after the impregnation and before the drying and calcination, an aging treatment may be carried out. Generally, the aging for impregnated catalyst precursor is performed at 20~30° C. for at least 1 hour, and usually at room temperature so as to further enhance stability of the aromatization catalyst.

The second modification treatment may be carried out after the completion of the active metal loading, or may be carried out simultaneously with the active metal loading, to further adjust acid property of the catalyst precursor. The second modification treatment may also be carried out by a conventional modification treatment process in the art, such as a impregnation method, e.g. an equal volume impregnation method.

In an embodiment of the present disclosure, the second modification treatment may introduce one or more of the elements of Group VA and lanthanide metals of the Periodic Table of the Elements for modification. When two or more elements are introduced, these elements may be introduced simultaneously or stepwise, for example, a salt solution in which two elements are simultaneously introduced is used for impregnation, and aging, drying, as well as calcination need to be performed after each impregnation.

In general, the aging may be performed at room temperature (20~30° C.) for at least 1 hour, usually 4~14 hours; the drying may be carried out at 80~150° C. for 4~12 hours; the calcination may be performed at a temperature of 400~600° C. for 2~8 hours.

It can be understood that in the two modification processes, reasonable control of the loading amount of the modifying elements is helpful to achieve the best performances of the aromatization catalyst. In actual production, the sum of the loading amounts of the modifying elements in the first modification treatment and the second modification treatment is generally controlled to be 0.5~8.0 wt %, and further controlled to be 0.5~5 wt %.

The present disclosure further provides an aromatization catalyst which is prepared according to the above preparation method. The aromatization catalyst prepared by the above preparation method has good carbon deposition resistance, thus has a long service life, and may maintain high aromatization activity for a long time, and enables an aromatization reaction can be steadily completed under mild conditions, and has a very high liquid yield on the premise of higher aromatic selectivity.

The present disclosure also provides an aromatization method, which comprising using the aromatization catalyst for aromatization of a gasoline raw material.

The above aromatization method may be carried out in a fixed bed reactor, that is, a fixed bed process may be adopted.

The aromatization catalyst provided by the present disclosure is especially suitable for aromatization of a gasoline fraction having a high olefin content, such as the fluid catalytic cracking gasoline, and the olefin content thereof is generally above 35 wt %. Usually a fluid catalytic cracking gasoline fraction from an initial boiling point to 130° C. is selected, for example, a fluid catalytic cracking gasoline fraction with a boiling range of 60° C.~100° C. is selected and subjected to aromatization.

The aromatization reaction may be completed under relatively mild conditions, usually under normal pressure (1 standard atmospheric pressure), a temperature of the aromatization reaction is 250~400° C., and a volume hourly space velocity of a gasoline fraction feed is 0.05~20 $h^{-1}$. Under these mild reaction conditions, the aromatization catalyst still has a very high activity, not only the selectivity of converting olefins to aromatics can be maintained above 60%, the liquid yield also can be maintained above 98.5%, and has a long single-pass life.

In an embodiment of the present disclosure, the temperature of the aromatization reaction is generally controlled at 300~400° C., and the volume hourly space velocity of a gasoline fraction feed is generally controlled at 0.05~5 $h^{-1}$, further 0.5 to 5 $h^{-1}$.

As indicated above, the aromatization catalyst according to the present disclosure is particularly suitable for the aromatization of FCC gasoline fractions having a high olefin content. When processing the FCC gasoline in the art, a FCC gasoline raw material is usually cut to realize the enrichment of olefins, for example, the fluid catalytic cracking gasoline is cut into three fractions of light, medium and heavy, wherein the olefin-enriched middle fraction has a boiling range of 60° C.~100° C.; then according to composition characteristics of each fraction, targeted desulfurization treatment is carried out, and a desulfurized light fraction, a desulfurized middle fraction and a desulfurized heavy fraction are respectively obtained; secondly, the above desulfurization middle fraction is further subjected to the above aromatization, and a desulfurization intermediate fraction having a high octane number is obtained; finally, the above desulfurized light, medium and heavy fractions are mixed to obtain a fluid catalytic cracking gasoline blending component with low sulfurs, low olefins and high octane number.

The disclosure finally provides a method for regenerating an aromatization catalyst, wherein the aromatization catalyst after being subjected to the aromatization reaction is dried under a nitrogen atmosphere at first, and then regenerated under an oxygen condition, wherein a temperature of the nitrogen is generally controlled at 400~700° C., a regeneration temperature is 400~800° C., an oxygen partial pressure is 0.2~0.6 kPa, a regeneration time is determined according to the carbon deposition amount of the aromatization catalyst, and usually the regeneration time is not less than 4 hours, usually 4~8 hours.

The inventors have found that the aromatization catalyst obtained through the regeneration still maintains high aromatization activity, and still enables the aromatization reaction to be stably completed under the above mild conditions, and achieves higher selectivity and very high liquid yield, and maintains a very good carbon deposition resistance, therefore, the aromatization catalyst can be used repeatedly.

A method for preparing an aromatization catalyst according to the present disclosure performs specific element modification treatment and active metal loading on a catalyst precursor obtained by mixing a zeolite molecular sieve and pseudoboehmite, the obtained aromatization catalyst has a high aromatization activity, which enables an aromatization reaction can be carried out under mild conditions of not higher than 400° C. and normal pressure, and achieves higher conversion of olefins to aromatic and a selectivity of above 60%, while ensuring the liquid yield is higher than 98.5%, and aromatics that produced are mainly C7~C9 aromatics, which is about 90%, and meanwhile the formation rate of benzene is low.

Moreover, the aromatization catalyst has good carbon deposition resistance, and thus has a long service life and stability, and its single-pass activity (the activity that maintains 50% olefin conversion rate) is 8~10 days and the liquid yield maintains above 98.5%, effectively avoiding oil quality loss and maintaining long-term stable operation;

Therefore, the aromatization catalyst not only can significantly reduce the olefin content, but also increase the aromatic content, especially the C7~C9 aromatic content in an aromatization product, and the benzene content is lower, thus the effect of low olefin, high octane number and low benzene content is achieved. And it is beneficial to obtain high-quality gasoline that meets the national VI standard, and at the same time, it is also conducive to saving production energy consumption, which thus has very good industrial amplification adaptability, and may be truly used in actual industrial production.

The regeneration method of the aromatization catalyst according to the present disclosure may realize regeneration of the aromatization catalyst by a simple oxidation-reduction, and the regenerated aromatization catalyst still has the above-mentioned good carbon deposition resistance and high aromatization activity. Therefore, it may be repeatedly used several times, saving production costs.

An aromatization method according to the present disclosure employs the above aromatization catalyst in an aromatization reaction, and may realize aromatization of olefins under mild reaction conditions of not higher than 400° C. and normal pressure, and has a very high liquid yield and aromatic selectivity, and is especially suitable for processing a fluid catalytic cracked gasoline having a high olefin content, which may not only save production energy consumption, but also significantly reduce olefin content and increase octane number, and the benzene content increases little, which facilitates to obtain high quality gasoline that meets the national VI standard; at the same time, the aromatization method has a long operating cycle and may be industrialized.

DESCRIPTION OF EMBODIMENTS

To make the objectives, technical solutions, and advantages of embodiments of the present disclosure clearer, the following clearly and comprehensively describes the technical solutions in embodiments of the present disclosure. Apparently, the described embodiments are merely a part rather than all embodiments of the present disclosure.

Example 1

This embodiment provides a method for preparing an aromatization catalyst, comprising the following steps of:

1. a nano-scale HZSM-5 molecular sieve with Si/Al ratio of 25 was physically mixed with pseudoboehmite at a ratio of 4:1 at room temperature to obtain a catalyst precursor.

2. an ion exchange modification of the catalyst precursor was performed by a method of constant temperature water bath, in particular, sodium hydroxide is dissolved in deionized water and mixed with the catalyst precursor to obtain a mixture, and then placing the mixture in a 90° C. water bath and stirring for 2 hours, so that the loading amount of sodium is about 0.2 wt %, a treated catalyst precursor is obtained, and then drying the treated catalyst precursor at about 120° C. for about 8 hours and calcining the treated catalyst precursor at about 540° C. for about 4 hours.

3. a first modification treatment of the catalyst precursor after the ion exchange modification is carried out by an equal volume impregnation method, in particular, dissolving ammonium dihydrogen phosphate in deionized water, and then impregnating the catalyst precursor, controlling a mass ratio of an aqueous solution of ammonium dihydrogen phosphate to the catalyst precursor to be (1.0±0.2):1, so that the loading amount of phosphorus is about 1 wt %; after the impregnation was completed, aging the resulting catalyst precursor at about 20° C. for about 6 hours, drying the catalyst precursor at about 120° C. for about 8 hours, and calcining the catalyst precursor at about 540° C. for about 4 hours.

4. a hydrothermally treatment of the catalyst precursor after the first modification treatment is conducted at a temperature of about 300° C. in a 100% steam atmosphere for about 6 hours. And then active metal loading of the hydrothermally treated catalyst precursor is carried out by an equal volume impregnation method, dissolving zinc nitrate in a 0.1 mol/L citric acid solution to obtain an impregnation liquid, and controlling a mass ratio of the impregnation liquid to the catalyst precursor after the hydrothermally treatment to be (1.0±0.2): 1, an impregnation temperature to be about 20° C., and an impregnation time to be about 10 hours, so that the loading amount of zinc is about 5 wt %; after the impregnation was completed, then aging the impregnated catalyst precursor at about 25° C. for about 4 hours, drying the impregnated catalyst precursor at about 120° C. for about 10 hours in an air atmosphere, and calcining the impregnated catalyst precursor at 540° C. for about 4 hours.

5. a second modification treatment of the active metal loaded catalyst precursor is carried out by the equal volume impregnation method so as to obtain the aromatization catalyst, referring to step 3 for detailed procedures, and the obtained aromatization catalyst was referred to as catalyst A.

Example 2

This embodiment provides a method for preparing an aromatization catalyst, and specific steps were basically the same as those of the Example 1, and the difference is:

During the active metal loading of step 4, the loading amount of zinc was about 8 wt %.

The aromatization catalyst finally obtained in Example 2 was referred to as catalyst B.

Example 3

This embodiment provides a method for preparing an aromatization catalyst, comprising steps of:

1. a nano-scale HZSM-5 molecular sieve with Si/Al ratio of 25 was physically mixed with pseudoboehmite at a ratio of 9:1 at room temperature to obtain a catalyst precursor.

2. an ion exchange modification of the catalyst precursor was performed by a method of constant temperature water bath, in particular, sodium hydroxide is dissolved in deionized water and mixed with the catalyst precursor to obtain a mixture, and then placing the mixture in a 90° C. water bath and stirring for 2 hours, so that the loading amount of sodium is about 0.5 wt %, a treated catalyst precursor is obtained, and then drying the treated catalyst precursor at about 120° C. for about 8 hours and then calcining the treated catalyst precursor at about 540° C. for about 4 hours.

3. a first modification treatment of the catalyst precursor after the ion exchange modification is carried out by an equal volume impregnation method, in particular, dissolving ammonium dihydrogen phosphate in deionized water, and then impregnating the catalyst precursor, controlling a mass ratio of an aqueous solution of ammonium dihydrogen phosphate to the catalyst precursor to be (1.0±0.2):1, so that the loading amount of phosphorus is about 1 wt %; after the impregnation was completed, aging the resulting catalyst precursor at about 20° C. for about 6 hours, drying the catalyst precursor at about 120° C. for about 8 hours, and calcining the catalyst precursor at about 540° C. for about 4 hours.

4. a hydrothermally treatment of the catalyst precursor after the first modification treatment is conducted at a temperature of about 300° C. in a 100% steam atmosphere for about 6 hours.

5. active metal loading of the hydrothermally treated catalyst precursor is carried out by an equal volume impregnation method: dissolving both ammonium dihydrogen phosphate and zinc nitrate in a 0.1 mol/L citric acid solution to obtain an impregnation liquid; controlling a mass ratio of the impregnation liquid to the catalyst precursor after the hydrothermally treatment to be (1.0±0.2): 1, an impregnation temperature to be about 30° C., an impregnation time to be about 15 hours, so that the loading amount of phosphorus is about 1 wt %, and the loading amount of zinc is about 5 wt %; after the impregnation was completed, then aging the impregnated catalyst precursor at about 28° C. for about 6 hours, drying the impregnated catalyst precursor at about 120° C. for about 8 hours in an air atmosphere, and calcining the impregnated catalyst precursor at 540° C. for about 4 hours so as to obtain the aromatization catalyst, which was referred as catalyst C.

Example 4

This embodiment provides a method for preparing an aromatization catalyst, and specific steps thereof were basically the same as those of the Example 1, and the differences were that:

In step 3, a first modification treatment of the catalyst precursor after the ion exchange modification is also carried out by an equal volume impregnation method, but a modification element used in the first modification treatment was lanthanum (La), in particular, lanthanum nitrate was dissolved in deionized water, so that the loading amount of lanthanum is 2 wt %, and aging was performed at about 23° C. for about 6 hours; then drying was performed at about 120° C. for about 8 hours, and finally calcination was performed at about 540° C. for about 8 hours.

The finally obtained aromatization catalyst was referred to as catalyst D.

Example 5

This embodiment provides a method for preparing an aromatization catalyst, and specific steps thereof are basically the same as those of the Example 1, and the differences were that:

In step 1, the mass ratio of HZSM-5 molecular sieve to pseudoboehmite was 9:1;

In step 3, a first modification treatment of the catalyst precursor after the ion exchange modification is also carried out by an equal volume impregnation method, but a modification element used in the first modification treatment was sodium (Na), in particular, sodium nitrate was dissolved in deionized water, a loading amount of sodium was controlled to be 0.5 wt %; and then aging was carried out at about 26° C. for about 6 hours; then drying was carried out at about 120° C. for about 8 hours, and finally calcination was carried out at about 540° C. for about 8 hours in turn.

The finally obtained aromatization catalyst was referred to as catalyst E.

Example 6

This embodiment provides a method for preparing an aromatization catalyst, and specific steps thereof are basically the same as those of the Example 1, and the difference was that:

In the active metal loading of step 5, the loading amount of zinc was 12 wt %.

The finally obtained aromatization catalyst was referred to as catalyst F.

Examples 7-12

FCC gasoline fractions of 60° C.~100° C. (an olefin content was 38.9 wt %, an aromatic content was 3.97 wt %)

as raw materials were subjected to aromatization reactions in a small fixed bed reactor, wherein aromatization catalysts used in Examples 7-12 were the aromatization catalysts prepared in Examples 1-6, namely, catalyst A to catalyst F, and aromatization reaction conditions were the same, which were 320° C., atmospheric pressure, volume hourly space velocity of 1 h$^{-1}$, reaction time of 30 h, reaction results were shown in Table 1.

Component analysis was performed on aromatics in the aromatization reaction products obtained in the above examples, wherein C6 aromatic (benzene) content was less, about 0.7~0.9 wt %, accounting for 3%~4% of a total mass of the aromatics; C7~C9 aromatic content was the highest, accounting for about 90% of the total mass of the aromatics, and the rest was aromatics of C10 and above.

Therefore, the aromatization reaction products may be used as a gasoline blending component, and meet the requirements for gasoline products in the national VI/Beijing VI automotive gasoline standards (GB17930-2016): olefin content ≤15~18 v %, aromatic content below 35 wt %, benzene content less than 0.8 wt %.

Example 13

A FCC gasoline fraction of 60° C.~100° C. (an olefin content was 38.9 wt %, an aromatic content was 3.97 wt %) as a raw material was subjected to an aromatization reaction in a small fixed bed reactor, wherein an aromatization catalysts used was the aromatization catalyst prepared in Example 1, namely, catalyst A, and aromatization reaction conditions were 320° C., atmospheric pressure, volume hourly space velocity of 1 h$^{-1}$, reaction time of 200 h, a reaction result was shown in Table 1.

Component analysis was performed on aromatics in the aromatization reaction products obtained in the above examples, wherein C6 aromatic (benzene) content was less, accounting for about 3% of a total mass of the aromatics; C7~C9 aromatic content was the highest, accounting for 90% of the total mass of the aromatics, and the rest was aromatics of C10 and above.

The aromatization reaction product may be used as a gasoline blending component, and meets the requirements for gasoline products in the national VI/Beijing VI automotive gasoline standards (GB17930-2016): olefin content 15 v %, aromatic content below 35 wt %, benzene content less than 0.8 wt %.

Example 14

The aromatization catalyst which subjected to the aromatization reaction in Example 13 was first dried at 500° C. in a nitrogen atmosphere, and then regenerated for 4 hours under regeneration conditions of a temperature of 550° C. and an oxygen partial pressure of 0.35 kPa so as to obtain a regenerated aromatization catalyst.

A FCC gasoline fraction of 60° C.~100° C. (an olefin content was 38.9 wt %, an aromatic content was 3.97 wt %) as a raw material was subjected to an aromatization reaction by using the regenerated aromatization catalyst in a small fixed bed reactor, and aromatization reaction conditions were 320° C., atmospheric pressure, volume hourly space velocity of 1 h$^{-1}$, reaction time of 200 h, a reaction result was shown in Table 1.

Component analysis was performed on aromatics in the aromatization reaction product obtained in this example, wherein C6 aromatic (benzene) content was less, accounting for about 3% of a total mass of the aromatics; C7~C9 aromatic content was the highest, accounting for 90% of the total mass of the aromatics, and the rest was aromatics of C10 and above.

Comparative Example 1

This embodiment provides a method for preparing an aromatization catalyst, and specific steps thereof are basically the same as those of the Example 1, and the difference was that:

the catalyst precursor was not subjected to the ion exchange modification of step 2, and directly subjected to steps 3, 4 and 5.

The aromatization catalyst finally obtained in Comparative Example 1 was referred to as catalyst G.

Catalyst G was evaluated using the same raw material and aromatization reaction conditions as that in Examples 7-12. The aromatization reaction lasted for 71 hours, and the catalytic activity basically kept stable. Through calculation, the liquid yield was 98.7% and selectivity was 63.00%. After reacted for 72 hours, the olefin conversion rate significantly decreased to 53%; continuing the reaction, the olefin conversion rate was decreased to 50% or less, so that a single-pass activity was only 3~4 days (the single-pass activity was an activity that olefin conversion rate maintains can be maintained at 50% or more).

Component analysis was performed on aromatics therein, wherein C6 aromatic (benzene) content was accounted for about 12% of a total mass of the aromatics; C7~C9 aromatic content was the highest, accounting for about 81% of the total mass of the aromatics, and the rest was aromatics of C10 and above.

Comparative Example 2

An aromatization catalyst was prepared in this comparative example according to the steps 1-2 and steps 4-5 in the Example 1, that is, after the ion exchange modification was carried out, without proceeding the first modification treatment, directly performing the hydrothermal treatment and active metal loading of the step 4, and the second modification treatment of step 5.

The aromatization catalyst finally obtained in Comparative example 2 was referred to as catalyst H.

Performances of the catalyst H were evaluated by using the same raw materials and aromatization reaction conditions as in Examples 7-12, and the reaction time was 30 hours, a reaction result was shown in Table 1.

As can be seen from Table 1, the liquid yield and selectivity were significantly decreased by using the aromatization catalyst obtained without the first modification treatment.

Comparative Example 3

An aromatization catalyst was prepared in the present comparative example according to the steps 1-4 of Example 1, and after the active metal loading was carried out, the second modification treatment was not performed.

The aromatization catalyst finally obtained in Comparative example 3 was referred to as catalyst I.

Performances of the catalyst I were evaluated by using the same raw materials and aromatization reaction conditions as in Examples 7-12, and the reaction time was 30 hours, a reaction result was shown in Table 1.

As can be seen from Table 1, the liquid yield and selectivity were significantly decreased by using the aromatization catalyst obtained without the second modification treatment.

Comparative Example 4

The present comparative example provides a method for preparing an aromatization catalyst, and specific steps thereof are basically the same as those in the Example 1, and the difference was that:

In step 4, the catalyst precursor after being subjected to the first modification treatment was directly subjected to the active metal loading without the hydrothermal treatment.

The aromatization catalyst finally obtained in Comparative example 4 was referred to as catalyst J.

Performances of catalyst J were evaluated by using the same raw materials and aromatization reaction conditions as in Examples 7-12, and the reaction time was 30 hours. A reaction result was shown in Table 1.

As can be seen from Table 1, the liquid yield and selectivity were significantly decreased by using the aromatization catalyst obtained without the hydrothermal treatment.

TABLE

| Example or Comparative Example | No. of catalyst | Liquid yield/ wt % | Product/wt % olefin | Product/wt % aromtic | Aromatic selectivity/% |
|---|---|---|---|---|---|
| Example 7 | A | 99.6 | 10.1 | 23.9 | 76.45 |
| Example 8 | B | 99.2 | 11.3 | 21.5 | 70.45 |
| Example 9 | C | 99.4 | 10.8 | 22.6 | 73.41 |
| Example 10 | D | 99.3 | 10.6 | 22.8 | 73.62 |
| Example 11 | E | 98.9 | 10.5 | 21.9 | 69.80 |
| Example 12 | F | 98.7 | 12.0 | 20.3 | 67.50 |
| Example 13 | A | 98.8 | 12.3 | 20.1 | 67.51 |
| Example 14 | A | 99.3 | 11.1 | 20.0 | 63.86 |
| Comparative Example 2 | H | 83.2 | 14.3 | 8.8 | 21.66 |
| Comparative Example 3 | I | 79.2 | 19.2 | 7.5 | 20.24 |
| Comparative Example 4 | J | 76.6 | 23.1 | 5.3 | 9.30 |

Finally, it should be noted that the foregoing embodiments are merely intended for describing the technical solutions of the present disclosure other than limiting the present disclosure. Although the present disclosure is described in detail with reference to the foregoing embodiments, persons of ordinary skill in the art should understand that they may still make modifications to the technical solutions described in the foregoing embodiments or make equivalent substitutions to some or all technical features thereof, and these modifications or substitutions do not make the essence of corresponding technical solutions departs from the scope of the technical solutions of embodiments of the present disclosure.

What is claimed is:

1. A preparation method for an aromatization catalyst, consisting of steps of:
    mixing a nano zeolite molecular sieve with a binder at a dry basis weight ratio of (1:9)~(9:1) to obtain a catalyst precursor;
    the catalyst precursor is successively subjected to an ion exchange modification and a first modification treatment, then subjected to a hydrothermal treatment, and further subjected to active metal loading and a second modification treatment, to obtain the aromatization catalyst; wherein
    an exchange element used for the ion exchange modification is at least one alkali metal selected from Group IA of the Periodic Table of the Elements, with a loading amount of 0.1~2 wt % based on a weight of the exchange element with respect to a weight of the catalyst precursor;
    a first modifying element used in the first modification treatment is at least one element selected from Group IA, Group VA, and lanthanide metals of the Periodic Table of the Elements, with a loading amount of 0.05~10 wt % based on a weight of the first modifying element with respect to the weight of the catalyst precursor;
    the active metal is at least one element selected from Group VIIB, Group VIII, Group IB and Group IIB of the Periodic Table of the Elements, with a loading amount of 0.5~25 wt % based on a weight of the active metal with respect to the weight of the catalyst precursor;
    a second modifying element used for the second modification treatment is at least one element selected from Group VA and the lanthanide metals of the Periodic Table of Elements, with a loading amount of 0.05~10 wt % based on a weight of the second modifying element with respect to the weight of the catalyst precursor.

2. The preparation method according to claim 1, wherein using a salt solution or an alkali solution containing sodium ions and/or potassium ions as an ion exchange solution to perform the ion exchange modification on the catalyst precursor, controlling the ion exchange modification is conducted at 60~120° C. for at least 30 minutes to obtain a treated catalyst precursor, then drying the treated catalyst precursor at 60~280° C. for at least 3 hours, and finally calcining the treated catalyst precursor at 450~700° C. for at least 1 hour.

3. The preparation method according to claim 1, wherein dissolving a metal salt of the active metal with 0.1~1.0 mol/L citric acid aqueous solution to prepare an impregnation liquid, and impregnating the catalyst precursor with the impregnation liquid to obtain an impregnated catalyst precursor, then drying and calcining the impregnated catalyst precursor so as to achieve the active metal loading; wherein,
    a mass ratio of the impregnation liquid to the catalyst precursor is (0.8~3.0): 1,
    the drying is performed at a temperature of 50~180° C. for no less than 2 hours; the calcination is performed at a temperature of 100~650° C. for no less than 2 hours.

4. The preparation method according to claim 1, wherein performing the hydrothermal treatment under a water vapor atmosphere performing at a temperature of 300~600° C. for at least 1 hour.

5. The preparation method according to claim 1, wherein sum of loading amounts of the first modifying element and the second modifying element is 0.5~8.0 wt % based on the weight of the catalyst precursor.

* * * * *